US010456219B2

(12) United States Patent
Buddemeyer et al.

(10) Patent No.: US 10,456,219 B2
(45) Date of Patent: Oct. 29, 2019

(54) ORTHODONIC POST AND PIN ASSEMBLY

(71) Applicants: Darren G. Buddemeyer, Ladue, MO (US); Matthew K. Malabey, Wentzville, MO (US)

(72) Inventors: Darren G. Buddemeyer, Ladue, MO (US); Matthew K. Malabey, Wentzville, MO (US)

(73) Assignee: ORTHO SOLUTIONS, LC, St. Ann, MS (US)

( * ) Notice: Subject to any disclaimer, the term of this patent is extended or adjusted under 35 U.S.C. 154(b) by 0 days.

(21) Appl. No.: 15/932,550

(22) Filed: Mar. 13, 2018

(65) Prior Publication Data

US 2018/0206943 A1    Jul. 26, 2018

Related U.S. Application Data

(63) Continuation-in-part of application No. 29/505,365, filed on Sep. 28, 2015, now Pat. No. Des. 794,804, which is a continuation-in-part of application No. 29/463,597, filed on Jan. 9, 2014, now Pat. No. Des. 749,737, application No. 15/932,550, which is a continuation-in-part of application No. 29/620,309, filed on Oct. 5, 2016, now Pat. No. Des. 848,001.

(60) Provisional application No. 62/601,738, filed on Mar. 29, 2017.

(51) Int. Cl.
*A61C 7/34* (2006.01)
*A61C 7/36* (2006.01)
*A61C 7/22* (2006.01)

(52) U.S. Cl.
CPC .................. *A61C 7/34* (2013.01); *A61C 7/36* (2013.01); *A61C 7/22* (2013.01)

(58) Field of Classification Search
CPC ................ A61C 7/34; A61C 7/36; A61C 7/22
See application file for complete search history.

(56) References Cited

U.S. PATENT DOCUMENTS

| 4,382,783 | A | | 5/1983 | Rosenberg | |
|---|---|---|---|---|---|
| 4,462,800 | A | * | 7/1984 | Jones ........................ | A61C 7/36 433/19 |
| 5,183,388 | A | * | 2/1993 | Kumar ..................... | A61C 7/36 433/19 |
| 5,439,378 | A | | 8/1995 | Damon | |
| D399,562 | S | | 10/1998 | Mendoza | |
| 6,036,488 | A | * | 3/2000 | Williams ................. | A61C 7/10 433/17 |
| 6,162,051 | A | | 12/2000 | Brehm et al. | |
| 6,193,508 | B1 | | 2/2001 | Georgakis | |
| 6,418,933 | B1 | * | 7/2002 | Strong .................... | A61F 5/566 128/848 |
| D531,015 | S | | 10/2006 | Lin | |

(Continued)

*Primary Examiner* — Ralph A Lewis
(74) *Attorney, Agent, or Firm* — Lewis Rice LLC (57) ABSTRACT

An orthodontic post and pin assembly including a post structure, being slotted at its back end, for accommodating a pin therethrough, the post includes a further slot into which the wire of an orthodontic appliance may locate, so that when the post and pin assembly are connected onto the wire, and a hybrid screw is tighten within the post, the appliance may become affixed to the wire at the position of its tightening and securement. This eliminates the need for removal of the wire, when a different or different size orthodontic appliance needs to be installed.

11 Claims, 5 Drawing Sheets

(56) References Cited

U.S. PATENT DOCUMENTS

| | | | |
|---|---|---|---|
| 7,267,545 B2 | 9/2007 | Oda | |
| 8,033,824 B2 | 10/2011 | Oda et al. | |
| 8,992,214 B2 | 3/2015 | Wu et al. | |
| D749,737 S * | 2/2016 | Buddemeyer | D24/156 |
| 9,393,085 B2 * | 7/2016 | Mohr | A61C 7/36 |
| 9,539,066 B2 * | 1/2017 | Dickerson | A61C 7/36 |
| 9,615,964 B2 * | 4/2017 | Rogers | A61F 5/566 |
| D794,804 S * | 8/2017 | Buddemeyer | D24/180 |
| 9,867,680 B2 | 1/2018 | Damon | |
| 10,201,450 B2 * | 2/2019 | Vincent | A61C 7/08 |
| 2006/0234180 A1 * | 10/2006 | Huge | A61C 7/36 433/19 |

* cited by examiner

ORTHODONTIC POST AND PIN ASSEMBLY

CROSS REFERENCE TO RELATED APPLICATION

This nonprovisional patent application claims priority to the provisional patent application having Ser. No. 62/601,738, filed on Mar. 29, 2017, which is a continuation-in-part of the design patent application having Ser. No. 29/505,365, filed on Sep. 28, 2015, and which application is a continuation-in-part of the patent application having Ser. No. 29/463,597, filed on Jan. 9, 2014, and now U.S. Pat. No. DES 749,737. This application is also a continuation-in-part of the application having Ser. No. 29/620,309, filed on Oct. 5, 2016.

FIELD OF THE DISCLOSURE

This invention generally relates to orthodontic appliances, usually of the type that are provided for furnishing enhanced teeth or jaw alignments, and more specifically pertains to an orthodontic post and pin assembly that can be applied to the orthodontic appliance, and can be easily removed or replaced, to obtain further adjustment to the appliance, without having to remove the mounting wire structure that was previously affixed to the various teeth, when the appliance was initially installed.

BACKGROUND

There are various orthodontic appliances that include select types of connectors, screws, pivots, and other installations that are integrated into the structure of the appliance, in order to facilitate its installation and usage. Many of these appliances require the application of connectors, that secure directly to the teeth and which have an alignment wire that extends through the various connectors, that can then support further parts of the appliance, such as biasing springs, that may be used to overcome an overbite, or for the application of a Herbst appliance, to attain movement of the jaw, particularly the mandibular jaw, in order to overcome an overbite condition. Frequently, when treating the patient, for a sustained period of time, it is a requirement that the entire assembly be disconnected, the wire freed from its locating through the connectors, for the purpose of installating perhaps a larger or smaller type of appliance, to attain the final finishing results for teeth or jaw movement, as may be required. In other words, if one Herbst appliance moves the jaw a certain distance, and to the extent that that Herbst appliance can achieve such, then it may be necessary to install a larger Herbst, to the patient, to attain even further shifting, and the type of jaw alignment as may be required for the treated patient. Or, if a spring mechanism is used, in order to provide for a shifting of teeth, or a collection of teeth, or to attain their better alignment, it may be that a different sized springs may be necessary to be installed in order to achieve such treatment. Heretofore, it was a requirement that usually the entire appliance must be removed, including its alignment and supporting wires, before a further sized appliance could be installed, to continue the treatment.

Examples of some of the components that may be used in the structure of the current invention can be seen in the United States patent of one of the inventors herein, Pat. No. Des. 749,737, that shows a Hybrid Screw for an Orthodontic Appliance, that may be applied to a post as used within the structure of this current invention, in order to achieve proper sustained usage of the appliance during the entire treatment procedure.

There are other types of appliances, and their methods of connections to the teeth, that are known in the art, for use in the orthodontic treatment of patients teeth.

Other types of snaps or screws that may be used in orthodontic appliances can be seen in the U.S. Pat. No. Des. 399,562. Pat. No. D531,015, shows a further threaded fastener.

Other examples of various types of orthodontic appliances that can be used to provide correction and treatment for malocclusions can be seen in the U.S. Pat. Nos. 4,382,783. 6,162,051, shows a further of correction appliance. These are all examples what exist in the prior art relating to this type of technology.

SUMMARY OF THE INVENTION

This invention primarily relates to an orthodontic post and pin assembly, that can be secured with the wire that is clasped onto the teeth of the patient, so that other appliances can be secured thereto, whether it be a Herbst appliance, or other means for providing for the expansion of teeth, alignment of teeth, or shifting of the jaw, when applied.

Heretofore, as previously reviewed, whenever an appliance has to be changed during the treatment of orthodontic malocclusions, the entire assembly, including its teeth applied wire, had to be totally disconnected, to allow for the application of a different sized appliance, or a different form of appliance, and then had to be totally reassembled also abinitio. The purpose of this invention is to provide a post and pin assembly that can secure directly onto the wire, and can be removed therefrom, for the application of another appliance, without having to disassemble the attached connector or clasp and its wire in the first instance.

Figure 9:
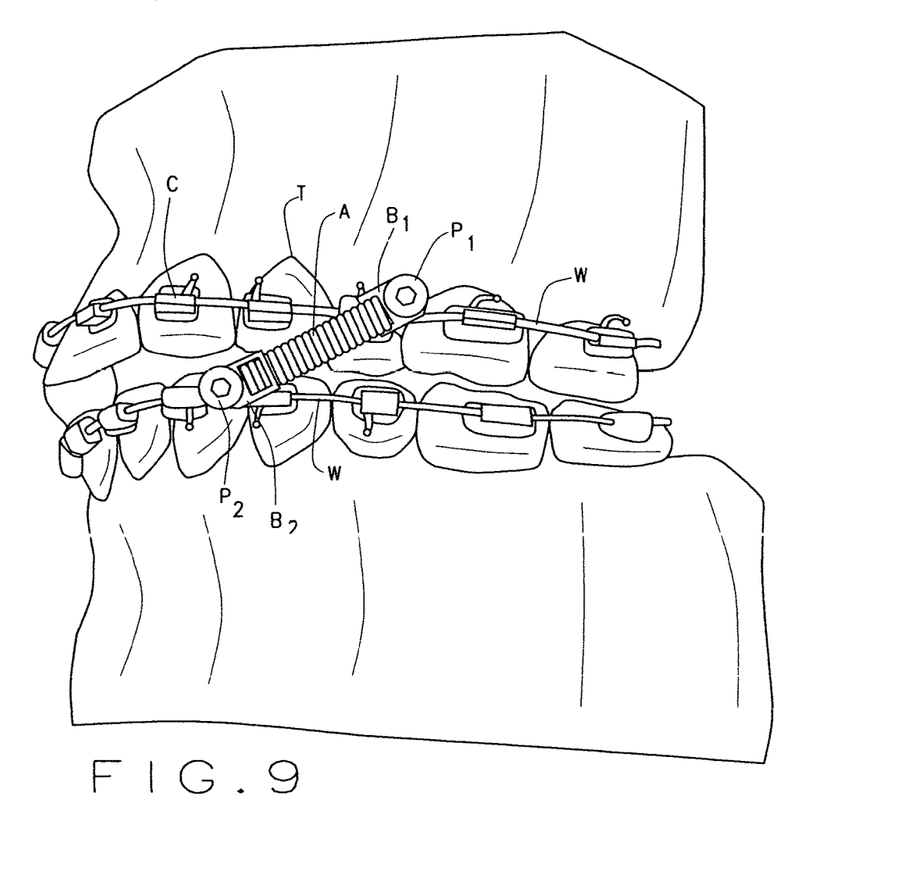
FIG. 9, as aforesaid, is a side view of a prior art installation of an orthodontic appliance.
Figure 10:
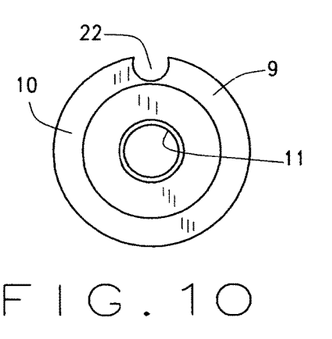
FIG. 10 is a front view of the post.
Figure 11:
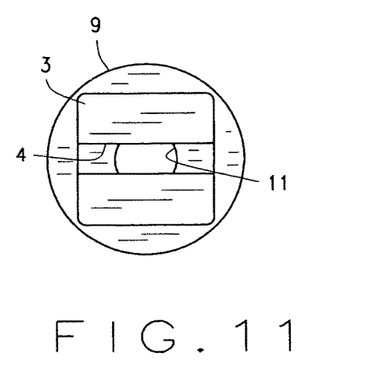
FIG. 11 is rear view of the post.
Figure 12:
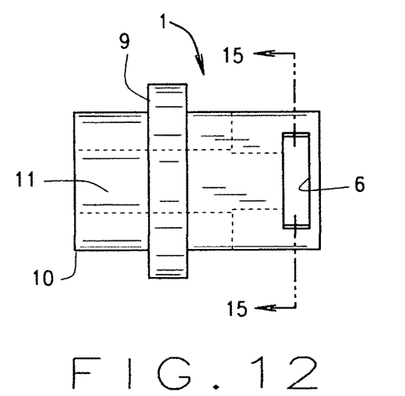
FIG. 12 is a bottom view.
Figure 13:
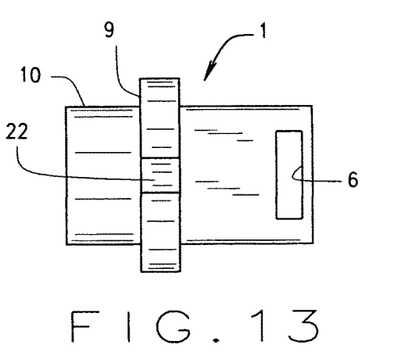
FIG. 13 is a top view.

As can be seen in FIG. 9, this is an example of a prior type of orthodontic assembly. As can be noted, the various clasps, as shown at C, have been cemented onto their respective teeth, as at T. Then, once the clasps are installed, an alignment wire W is applied to and through each clasp, and provides the basic support for the application of an orthodontic appliance, as noted at A, secured onto their respective wires, by their pivots P1 and P2, as known in the art. But, these pivots, on their inner ends (not shown) have an aperture therethrough, and through which the wire W locates, when the appliance is installed. In this particular instance, the appliance is a spring member, as noted, and which may be designed for movement of the lower jaw, relative to the upper jaw, during its application and usage during a dental treatment. As explained, when the appliance A had to be changed, it could not be directly removed from its support wire W, but the entire wire W had to be withdrawn from its various clasps C, pulled free from the pivots P1 or P2, and then a new appliance could be installed, the wires reapplied to their respective clasp, in order to continue the treatment process. This is very time consuming, as can be easily understood.

The current invention utilizes a post and pin assembly, that can be separated, so the wire can be inserted into the post, and then secured into position by means of its pin, so that the wire, as applied to its various clasps, can remain in situ, and the wire does not have to be withdrawn from its various clasp, when an appliance utilizing the post and pin connection of this current invention is used. The post includes a rear segment that has a slot provided therein, and further includes a perpendicularly oriented further slot, through both legs of the post, and into which and through the pin can insert, in order to lock the guide wire in place, within the post and pin assembly. The post has an integral sleeve at its approximate midpoint, along its length, and then has an integral cylindrical or the like portion extending forwardly therefrom, which has an internal aperture, threaded as noted, and which can receive an orthodontic screw that serves a two fold purpose. One, it extends through the post, when the screw is threaded therein, and secures against the orthodontic wire, and presses it into a fixed position against the attached pin, to hold the post and its pin to the wire at a precise location, determined by the orthodontist. Secondly, the screw has a sufficiently sized head in order to extend circumferentially beyond the cylindrical portion of the post, so as to confine and locate thereon the extending bearing portions, as noted at B1 and B2, of the orthodontic spring of the appliance A, as reviewed in FIG. 9. Thus, the screw, in combination with the post and pin, provides a means for securement of the orthodontic appliance A to the assembly, during its application and usage.

Then, when it becomes necessary to apply a different orthodontic appliance, or one of a greater or lesser size to the wires W, all the practitioner needs to do is to remove the screw, and pull free the pin from its post, and the post, and its applied appliance, can be easily removed from the wire, without any interference. The wire itself does not have to be removed from its various clasps, but can remain in position, which substantially reduces the time for treatment of the patient, and the application and removal of the various appliances, not to mention to the extra costs involved, during treatment.

It is, therefore, the principal object of this invention to provide a post and pin assembly that can be used for readily applying or removing orthodontic appliances to the teeth, during treatment.

Another object of this invention is to provide a post, and a cooperating pin, that can be inserted in the post, to hold the orthodontic wire precisely therein, during installation and usage of an appliance.

Still another object of this invention is to provide a post and a conveniently separable pin that may be removed by the orthodontist, when applying an appliance to its wire, or removed therefrom, during a treatment session.

Still another object of this invention is to provide an orthodontic post that can easily hold into position, any orthodontic appliance, and allow for its relative minuscule pivot during the application and usage of the appliance during treatment.

Still another object of this invention is to provide an orthodontic post that can cooperate with a hybrid screw that provides different functions during the application and usage of the assembly when treating a patient's teeth.

Another object of this invention is to provide an orthodontic pin that is uniquely shaped to provide for its ease of insertion or removal into its cooperating post, for holding a wire in position, but has a facility for ease of removal, when the appliance is either disassembled, or when a different sized or type of appliance needs to be installed, during a treatment session.

A further object of this invention is to provide an orthodontic pin that has various integrated structures that securely hold it to the post to which it is applied, and has integral structure that both inserts into and embraces the back end of the post, to assure that the pin remains in place once installed, and during usage.

These and other objects may become more apparent to those skilled in the art upon review of the summary of the invention as provided herein, and upon undertaking a study of the description of its preferred embodiments, in view of the drawings.

DETAILED DESCRIPTION OF PREFERRED EMBODIMENTS

Figures 1, 2:
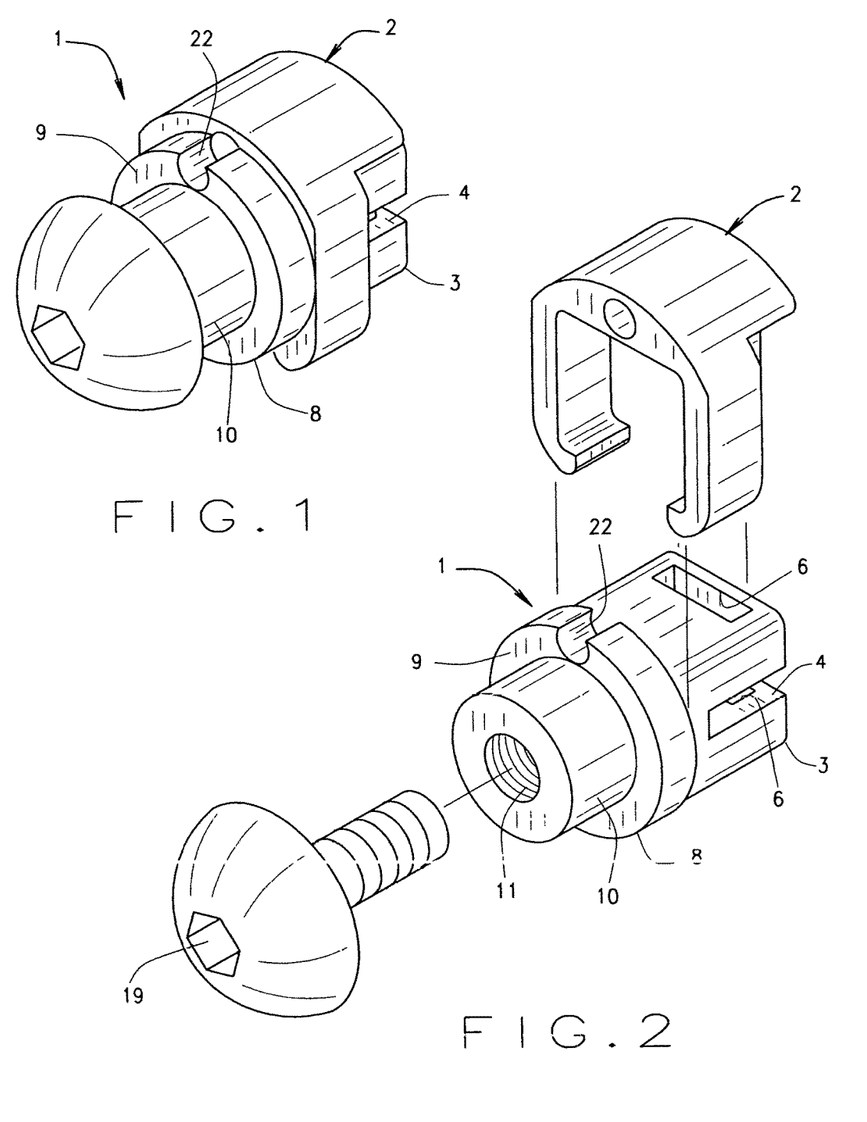
FIG. 1 is an isometric view of the post and pin assembly of this invention.
FIG. 2 is an isometric view of the post, with the pin separated therefrom, during installation or removal of the assembly.
Figure 14:
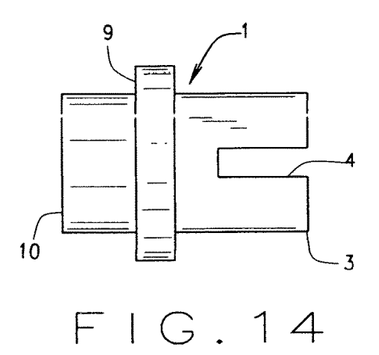
FIG. 14 is a right side view of the post, the left side view being a mirror image thereof.
Figure 15:
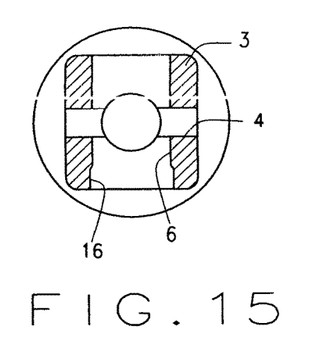
FIG. 15 is a sectional view taken along the line 15-15 of FIG. 12.
Figure 16:
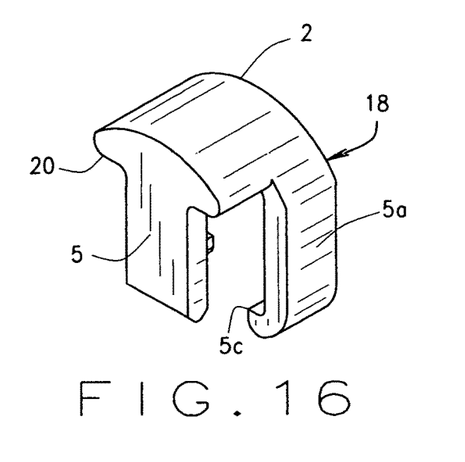
FIG. 16 is a front view of the pin of the assembly.
Figure 17:
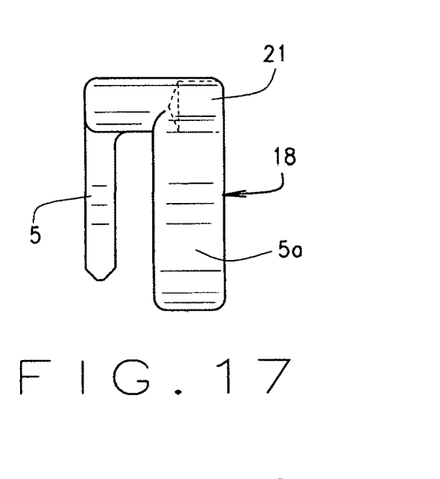
FIG. 17 is a right side view of the pin, the left side view being a mirror image thereof.
Figure 18:
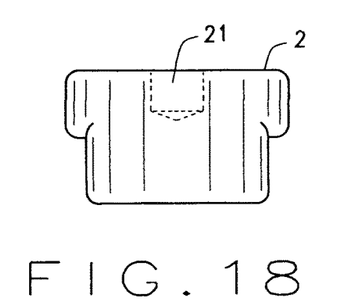
FIG. 18 is a top view.
Figure 19:
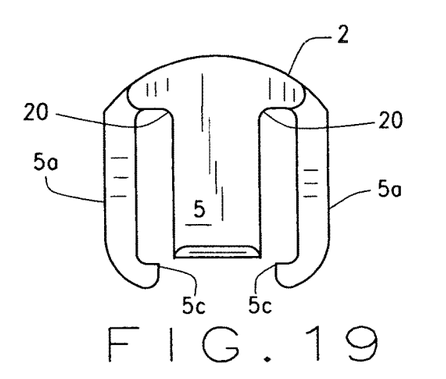
FIG. 19 is a back view.

In referring to the drawings, and in particular FIG. 1, it can be seen that the orthodontic post 1, and its cooperating pin 2 are disclosed assembled together as during usage. As noted in FIG. 2, the pin 2 is disclosed being separated from its post 1, as when the assembly is being installed, or removed, from one of the wires W, during its installation or usage. While the pin is identified as such, it also includes a clamping portion that provides for securement of the pin when it is installed upon the post in preparation for application and usage. As can be noted, the post includes a rear segment, as at 3, and which is laterally slotted, as noted at 4, and which extends all the way across the segment 3, as also can be noted in FIGS. 6 and 14. Thus, as also noted, the pin 2, particularly at its lower portion 5, (see FIG. 3) extends downwardly through the vertical opening 6 of the post, as can also be seen in the variety of Figures. Thus, when the pin is fully inserted within the rear segment 3 of the post, it forms an opening, as at 7, (see FIG. 6) between the post and pin, and it is through this opening that the wire W is positioned, when a post is applied for supporting any type of orthodontic appliance A, of the type as previously explained in FIG. 9.

Figures 3, 4, 5, 6:
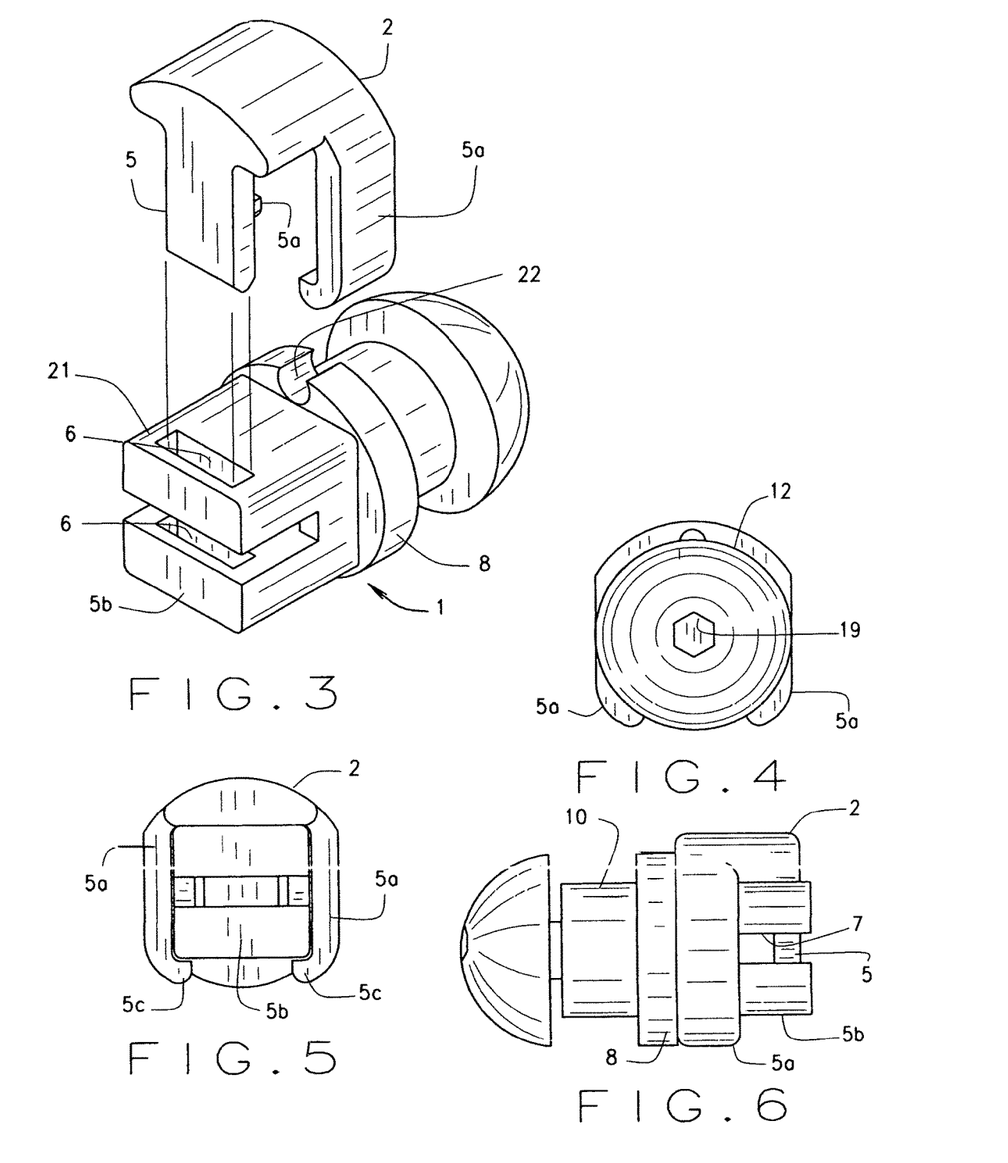
FIG. 3 is an isometric exploded view showing the post and pin assembly from the approximate rear, with the pin being removed from its post.
FIG. 4 is a front view of the assembly of FIG. 1.
FIG. 5 is a rear view of the assembly of FIG. 1.
FIG. 6 is a right side view, the opposite side view being a mirror image thereof.
Figure 7:
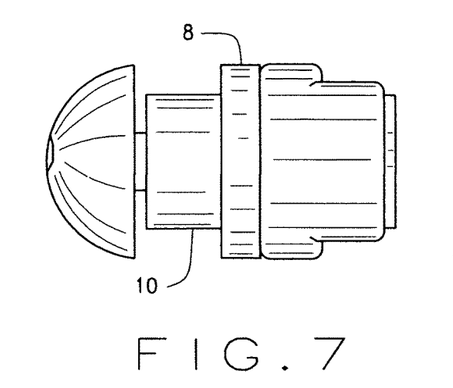
FIG. 7 is a top view.
Figure 8:
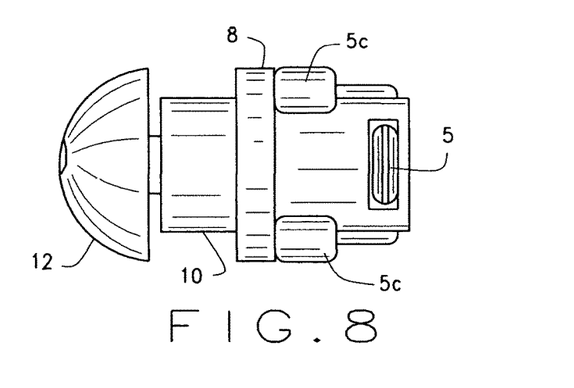
FIG. 8 is a bottom view.

The pin also has integral side braces 5a, one on either side, that embrace and secure under the lower part 5b, of the post 1, as can be seen in FIGS. 4 and 6. The lower end of these braces 5a are inturned, as at 5c, to embrace the bottom part of the post 5b, as noted also in FIG. 5.

As can also be noted, the pin may also have integral extending flanges 20, and these flanges are for engagement with the upper surface of the post, as at 21, when the pin is fully installed for securement of the wire W, therein, during its usage.

As also noted in FIG. 5, the pin 2 and its lower portion 5 extends all the way through the slot 6 formed in the rear segment of the post, and further closes the slot 4 that is readily disposed laterally across the back of the post, and into which the wire W inserts, during its installation, or when removed therefrom. Obviously, as can be seen in FIGS. 1 and 6, when the post 2 is installed, it fully closes off the slot 7, particularly once the wire W inserts therein. And, when the pin is removed, as noted in FIGS. 2 and 3, the slot 4 opens for either the insertion, or removal, of the wire W, during its processing either while being installed, or removed, as previously explained.

Figure 20:
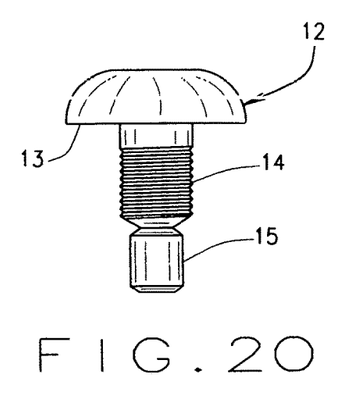
FIG. 20 shows a front view of a hybrid screw used in conjunction with the orthodontic post and pin assembly of this invention.

At the midpoint of the post 1, as noted in FIGS. 1, 2, 3, and 6 through 8, there is an integral sleeve like part 8, which is larger than the diameter or outer dimensions of the other segments of the post, and this provides a base, as at 9, against which the bearing portions B1 or B2 of any appliance may move or pivot against, when positioned during the installation or usage of any appliance A, with this assembly. In addition, the post has an integral forwardly extending cylindrical portion 10, and the cylindrical portion engages for pivotal movement of the appliance A, or its bearinged ends B1 and B2, when the appliance is installed thereon. Furthermore, interiorly of the cylindrical portion is a central aperture 11, herein noted as being threaded, and into which one of the hybrid type of orthodontic screws, of the type as shown at 12 in FIG. 20 may insert, and be threadedly engaged therein, so that the upper flanged portion 13 on the screw will extend beyond the circumference of the cylindrical portion 10, and act as a fastening means for holding the bearinged portions of the appliance A, onto the post, during its assembly and usage. See FIG. 6. In addition, when the threaded part 14 of the hybrid screw is engaged within the cylindrical portion 10, as aforesaid, its integral post 15 will extend into the position of the clearance area 7 (see FIG. 6) and force any wire W located therein to bias against the pin 2, and particularly its lower portion 5, and secure and affix the appliance, and the post, relative to its precise installation upon the wire W, during installment of the appliance for a future orthodontic correction of the patient's teeth.

As can be seen in FIGS. 10 through 15, the structure of the post 1, itself, is readily disclosed. What should be noted, though, as in FIG. 13, in addition to FIG. 2, is that the vertical opening 6 provided through the rear segment 3 of the post extends all the way therethrough, and at its lower end has a slight flare, as at 16, as noted. Then, the pin 2 may have a slight extension, not shown, extending outwardly, and this extension 17, of the pin, is designed for snap engagement within the flared portion 16, of the post slot, for securement of the pin with the post, once installed. As can further be noted in FIGS. 16 through 19, the pin may further include a series of integral side braces 18, that integrally extend down, as noted at 5a, from the top portion of the pin 2, laterally, and which can snap engage to the bottom part 5b of the post, through the application of those inturned portions 5c, that embrace the post, as can be noted in FIG. 5. Thus, the pin 5 extends down through the various slots 6 of the post, and at the same time, its lateral braces 5a will snap engage underneath of the post, as noted, in order to retain the pin in place. Thus, in that manner, the pin is fully engaged upon the post, during its application for orthodontic purposes. In addition, when it is desired to remove the pin from the post, its legs 5a will be expanded outwardly, through pressure, or the use of a tool, so that its inturned portions 5c clear the bottom part of the post 5b, to allow the pin to be elevated, and removed, when the orthodontic appliance is being readjusted.

Both the post and the pin, usually, will be made of steel, such as stainless steel, or perhaps out of harden polymer, such as polypropylene, or the like, during their formation.

As can further be noted, the screw 12 as in FIG. 4, may have a hex or other shape cut out portion, as at 19, in order to accommodate a tool, or screw driver, when applying the screw to the orthodontic appliance, or for its removal.

Also, as can be seen, the pin may have slight flares, as at 20, so as to limit the extent of application of the pin through the post, when installed. In addition, there may be an aperture, as at 21, provided upon the face of the pin, and into which a tool may be installed, or it may be threaded for application of a threaded tool, in order to aid in the removal of the pin when required during treatment. In addition, the integral sleeve 8 of the post 1 may include a clearance slot 22, to accommodate the insertion of a tool during its usage.

The foregoing provides a general definition, description, and embodiment for the structure of the assembly of this current invention. As stated, it greatly facilitates the application, removal, and reinstallation of any orthodontic appliance, to the orthodontic wires secured to the teeth of the patient, without requiring any further removal of the wiring, as previously required in the prior art structures, and their usage and application in furnishing orthodontic treatment to the patient.

Variations or modifications to the subject matter of this invention may occur to those skilled in the art upon review of the invention as described herein. Any variations, if within the spirit of this invention, are intended to be encompassed within the scope of any claims to patent protection issuing herein. The description of the preferred embodiment of the invention, as aforesaid, and its depiction in the drawings, are primarily set forth for illustrative purposes only.

What is claimed is:

1. An orthodontic post and pin assembly, said orthodontic post having a rear segment, an integral sleeve at its intermediate location, and a cylindrical portion extending integrally forwardly from said sleeve, said cylindrical portion having an aperture provided centrally therethrough, for accommodation of a hybrid screw during installation of the assembly onto the wire portion of an orthodontic appliance, said cylindrical portion and sleeve of the post provided for accommodating a bearing surface of a Herbst orthodontic mechanism or a spring biasing orthodontic member, the rear segment of the post having a lateral slot therethrough, and into which an orthodontic wire may be located during installation of the assembly, said rear segment of the post also having a vertical slot provided therethrough, and for accommodating the insertion and retention of said pin therethrough, when the assembly is installed onto the wire of an orthodontic appliance during installation and treatment of a patient, said pin includes a head portion, a downwardly extending portion that extends through the vertical slot of said post, and said pin having a pair of lateral braces, that embrace the sides of the post when the pin is installed for application for retaining an orthodontic wire therein.

2. The assembly of claim 1, wherein said aperture of the cylindrical portion of the post is threaded.

3. The assembly of claim 2, wherein the lateral slot at the rear segment of the post extends fully across the said rear segment.

4. The assembly of claim 3, wherein said vertical slot extends fully vertically through the rear segment of said post.

5. The assembly of claim 4, wherein the lateral slot and the vertically arranged slot through the rear segment of the post intersect.

6. The assembly of claim 5, wherein said post and pin are formed of stainless steel.

7. The assembly of claim 5, wherein said post and pin are formed of a polymer.

8. The assembly of claim 1, wherein the bottom edges of the lateral braces of the pin are inturned, for engaging the bottom surface of the post, for securement of the pin in place during its installation.

9. The assembly of claim 8, wherein said pin, proximate its upper segment, has a structure provided thereat to facilitate the removal of the pin during installation or removal of the assembly from any supportive orthodontic wire.

10. The assembly of claim 9, wherein said structure includes an aperture provided through the upper portion of the pin, and to which a tool may be applied for facilitating the installation or removal of the said pin from its post.

11. The assembly of claim 1, and including a hybrid screw, provided for engagement within the cylindrical portion of the said post, and extending into the lateral slot at its rear segment, to bias against and affix the post relative to the orthodontic wire to which said post is precisely installed.

* * * * *